(12) United States Patent
Pratt

(10) Patent No.: US 6,322,250 B1
(45) Date of Patent: Nov. 27, 2001

(54) X-RAY CHAIR

(76) Inventor: Miriam M. Pratt, 178 Morrison Ave., Staten Island, NY (US) 10310

( * ) Notice: Subject to any disclaimer, the term of this patent is extended or adjusted under 35 U.S.C. 154(b) by 2 days.

(21) Appl. No.: 09/604,638

(22) Filed: Jun. 27, 2000

(51) Int. Cl.$^7$ .................................................. A61G 15/00
(52) U.S. Cl. ........................... 378/208; 378/68; 378/179; 280/250.1; 280/650; 297/344.1; 297/344.21
(58) Field of Search ..................................... 378/208, 209, 378/177, 178, 179, 68, 20; 280/647, 650, 250.1; 297/344.21, 344.1, 314, 325, 344.12, 344.13, 344.14, 344.16

(56) References Cited

U.S. PATENT DOCUMENTS

| | | | |
|---|---|---|---|
| 3,585,386 | 6/1971 | Horton | 250/50 |
| 3,626,186 | 12/1971 | Allard | 250/50 |
| 3,628,829 | * 12/1971 | Heilig | 297/217 |
| 4,699,425 | 10/1987 | Ohlson | 297/349 |
| 4,831,644 | 5/1989 | Lopez | 378/178 |
| 5,613,738 | * 3/1997 | Britton | 297/467 |
| 5,713,591 | 2/1998 | Zarkhin et al. | 280/250.1 |
| 6,068,280 | * 5/2000 | Torres | 297/314 |
| 6,089,593 | * 7/2000 | Hanson et al. | 280/650 |
| 6,106,065 | * 8/2000 | Carroll | 297/330 |

* cited by examiner

*Primary Examiner*—Robert H. Kim
*Assistant Examiner*—Drew A. Dunn
(74) *Attorney, Agent, or Firm*—Goldstein Law Offices, P.C

(57) ABSTRACT

An x-ray chair, for providing support and comfort to a patient seated therein during an x-ray procedure, comprising a patient carrier and a lower mobility assembly. The patient is seated within the patient carrier, and the lower mobility assembly allows the patient carrier to rotate (via a lazy susan arrangement), tilt forwards and backwards, and tilt sideways. Various adaptations are provided on the patient carrier to maximize the comfort and support for the patient, including removable support pillows, a removably pummel, retractable leg supports, and multipositional arm rests.

3 Claims, 6 Drawing Sheets

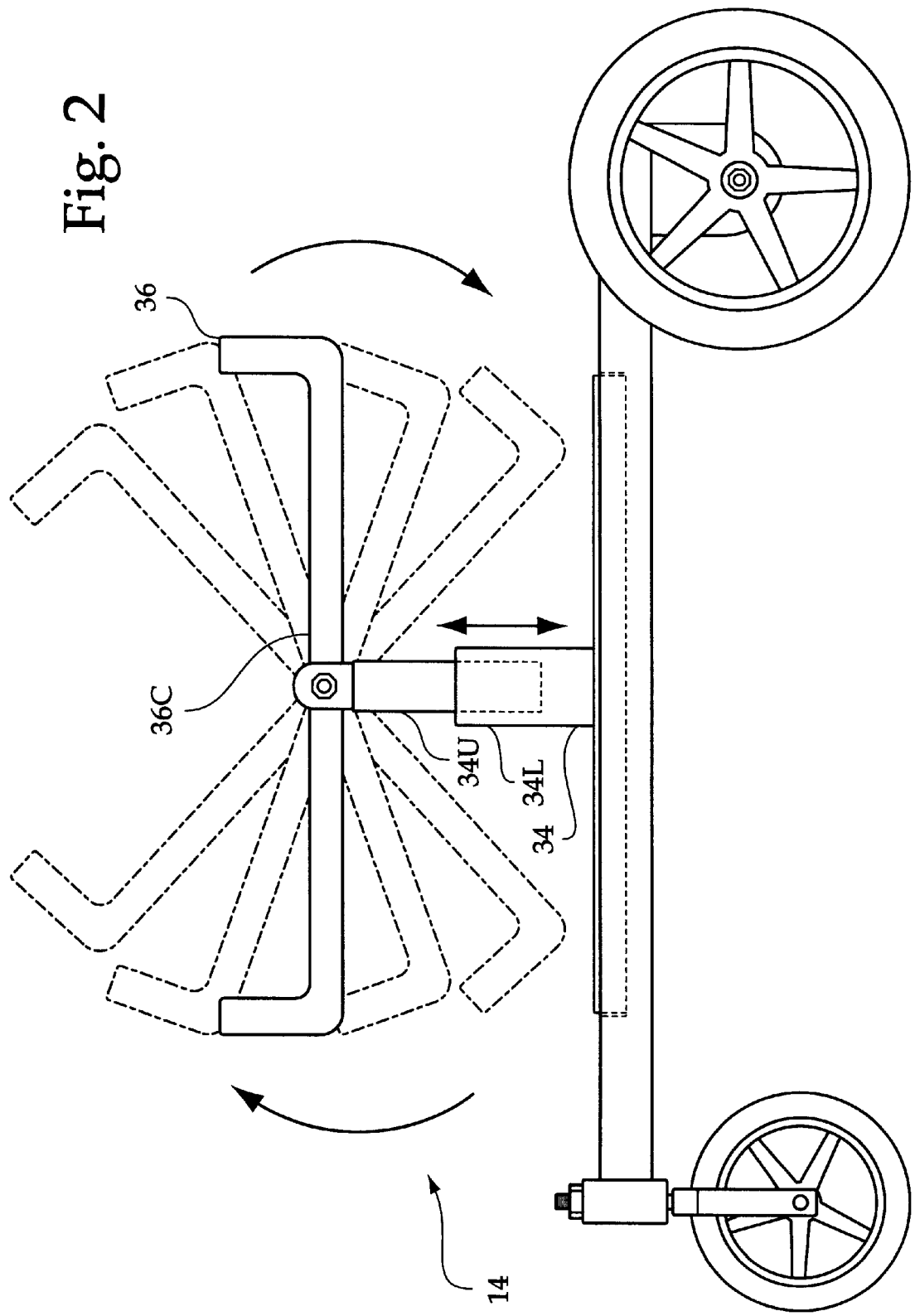

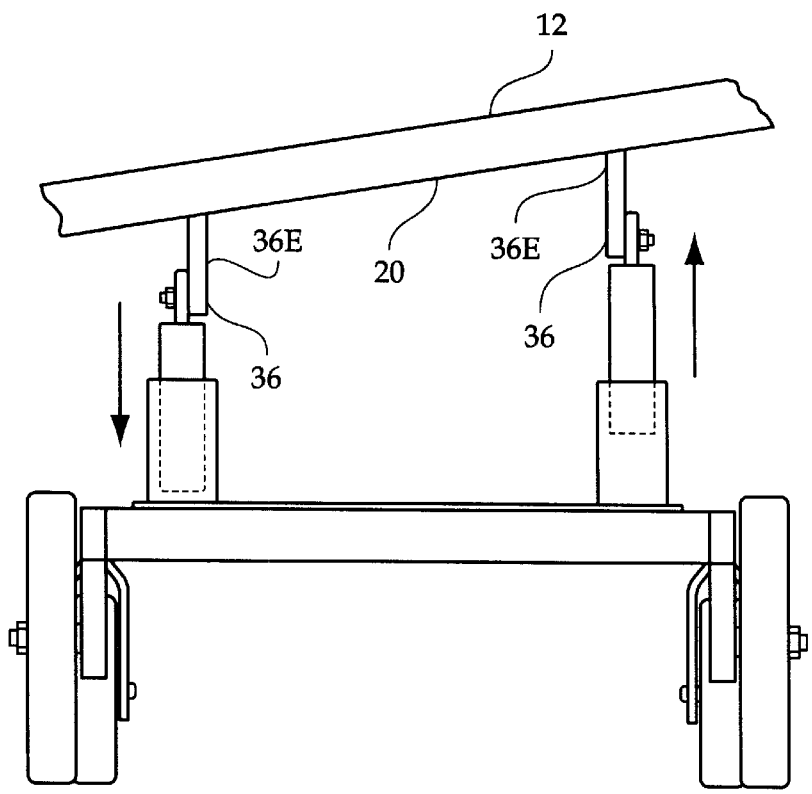
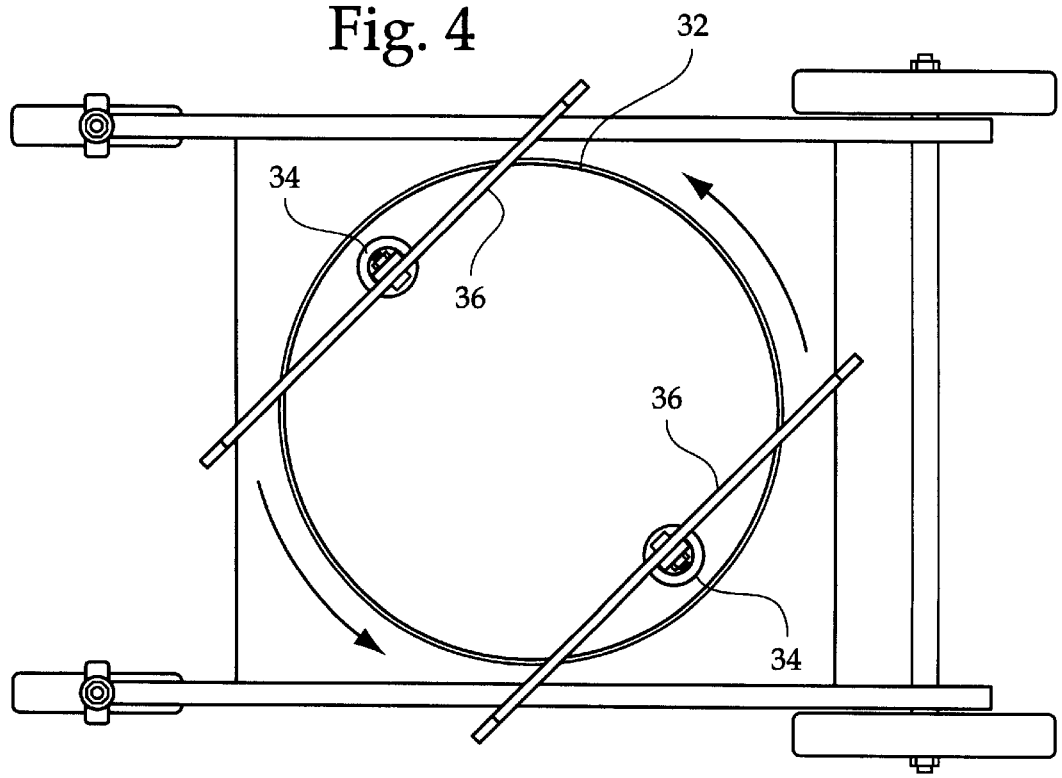

X-RAY CHAIR

BACKGROUND OF THE INVENTION

The invention relates to an x-ray chair. More particularly, the invention relates to a chair which allows a person to be comfortably and properly positioned for an x-ray examination.

A variety of medical procedures require that the patient remain still in a specific position. In particular, x-ray examinations generally require that the patient remain motionless for a second or more. In addition, such examinations require that the patient be positioned in such a manner that a useful image of the relevant anatomy can be acquired.

Certain patients are notoriously difficult to position. In particular, pediatric, geriatric, and developmentally disabled patients can have difficulty entering a position required for a proper x-ray examination, and maintaining the position long enough for a non-blurred image to be acquired.

One type of x-ray examination where difficulty is often experienced is a modified barium swallow study. In this study, the swallowing sequence is evaluated to determine what modifications and techniques are necessary to ensure a safe swallow. Unfortunately, many individuals with even mild physical and developmental disabilities cannot undergo the modified barium swallow study because of inability to optimally position these individuals.

Various chairs and devices have been developed in an attempt at holding a patient in position for various medical purposes. Unfortunately, these devices tend to focus on the use of restraints and shackles to hold the patient in place, and do not place enough emphasis on the comfort and safety of the patient.

While these units may be suitable for the particular purpose employed, or for general use, they would not be as suitable for the purposes of the present invention as disclosed hereafter.

SUMMARY OF THE INVENTION

It is an object of the invention to provide an x-ray chair which allows a patient to be properly positioned for an x-ray examination and maintained in that position during the examination. Accordingly, the chair has several axis of tilt, and has numerous adaptations which allow the patient to be positioned as desired. The chair can be quickly customized and adapted to properly position the patient within minutes immediately prior to the x-ray examination.

It is another object of the invention to provide an x-ray chair which is comfortable to the patient, and does not unduly restrain the patient. Accordingly, the various positioning adaptations of the chair provide support to the patient in order to maintain the position of the patient without actually restraining the patient.

It is a further object of the invention to provide an x-ray chair which helps a patient feel at ease during the x-ray examination. Accordingly, by positioning the patient in a proper, yet comfortable position without restraints, the patient is likely to feel at ease and will likely perform as needed during the examination procedure.

It is a further object of the invention to provide a chair which is versatile, providing numerous applications. Accordingly, the chair may be used to position the patient during a variety of different x-ray procedures. In addition, the chair is provided with mobility through a series of wheels. The wheels allow the chair to be used as a transport chair to bring the child to the x-ray room, building, or hospital, while providing optimum positioning which allows the patient to be transported in optimum comfort.

The invention is an x-ray chair, for providing support and comfort to a patient seated therein during an x-ray procedure, comprising a patient carrier and a lower mobility assembly. The patient is seated within the patient carrier, and the lower mobility assembly allows the patient carrier to rotate, tilt forwards and backwards, and tilt sideways. Various adaptations are provided on the patient carrier to maximize the comfort and support for the patient, including removable support pillows, a removably pummel, retractable leg supports, and multipositional arm rests.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 2 is a side elevational view thereof, indicating various types of motion made possible by said lower mobility assembly.

FIG. 3 is a front elevational view thereof, indicating other types of motion possible thereby.

FIG. 4 is a top plan view thereof, indicating further types of motion possible thereby.

DETAILED DESCRIPTION OF THE PREFERRED EMBODIMENTS

Figure 5:
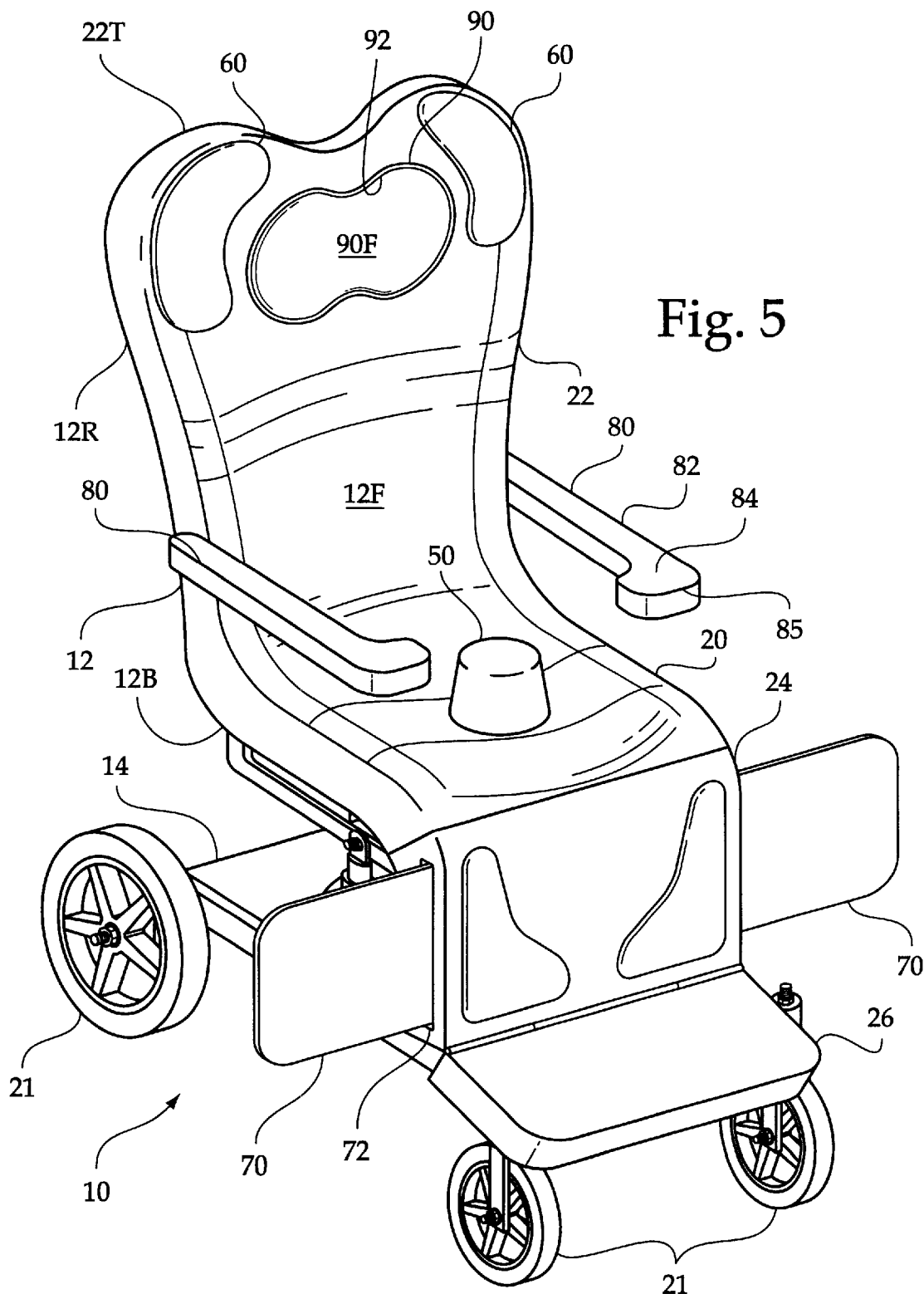
FIG. 5 is a diagrammatic perspective view, showing the invention, per se.

FIG. 5 illustrates an x-ray chair 10, for use in seating a patient during an x-ray examination. The x-ray chair comprises a patient carrier 12, and a lower mobility assembly 14. The patient carrier 12 is adapted to allow the patient to be seated thereon and provide ideal comfort, support, and positioning to said patient. The lower mobility assembly 14 is adapted to provide various axis of tilt and rotation for the patient carrier 12. In addition, the lower mobility assembly 14 provides locomotion for the entire x-ray chair 10 through the use of wheels 21.

The patient carrier 12 may be considered to have a seat portion 20, a seat back 22, a calve support 24, and a foot rest 26. The patient carrier 12 includes a patient carrier front surface 12F, which is contiguous throughout the seat portion 20, seat back 22, calve support 24, and foot rest 26. The patient carrier 12 also has a rear surface 12R extending parallel to the front surface 12F and fully opposite therefrom. In addition, the rear surface 12R includes a bottom surface 12B which is that portion of the rear surface 12R extending beneath the seat portion 20.

Figure 1:
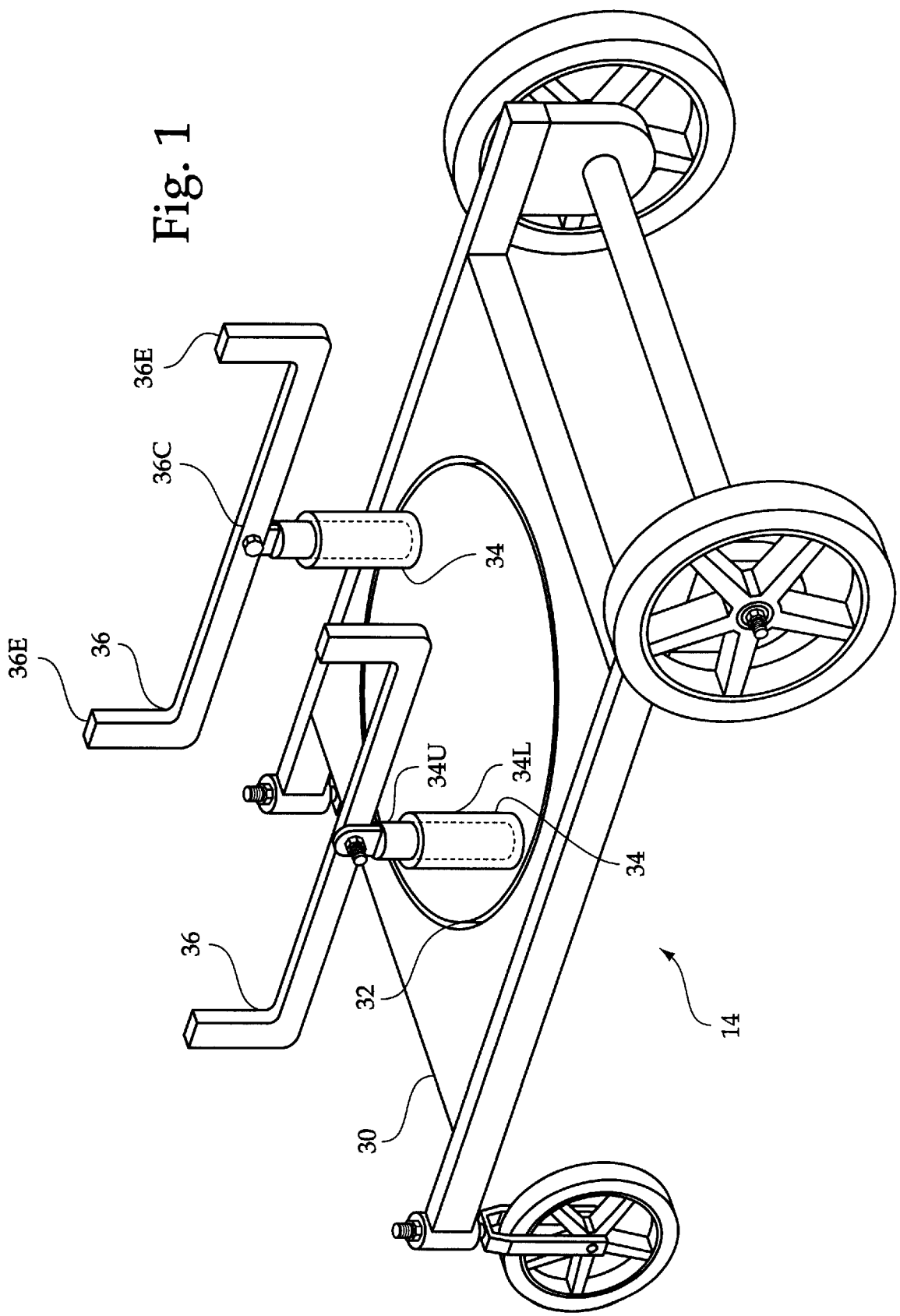
FIG. 1 is a diagrammatic perspective view, illustrating the lower mobility assembly of the invention.

Referring now to FIG. 1, the lower mobility assembly 14 has various adaptations to provide tilting and rotation of the patient carrier. These various adaptations may be configured in many different ways while still providing the same type of tilting and rotation. Accordingly, the mechanisms shown in FIG. 1 through FIG. 4 is illustrative only of one mechanism which will accomplish the goals of the invention.

In particular, the lower mobility assembly 14 includes a base 30. Mounted upon the base 30 is a lazy susan 32. Mounted to the lazy susan 32 are a pair of vertical supports 34.

The vertical supports 34 are diametrically opposed on said lazy susan 32. Each vertical support 34 has a vertical support upper 34U and a vertical support lower 34L. Each of the vertical support uppers 34 is adjustable with respect to its associated vertical support lower 34L to adjust the relative heights of the vertical supports 34.

A pair of U-arms 36 are mounted to one of the vertical support uppers 34U. Each U-arm has a U-arm center 36C and a pair of U-arm ends 36E. Each U-arm center 36C is pivotally mounted to one of the vertical supports 34 such that said U-arm 36 is capable of pivotal motion with respect to the horizontal, such that the U-arms 36 remain parallel to each other in their respective vertical planes. The U-arm ends 36E are all mounted to the bottom surface 12B of the patient carrier 12 such that each of the U-arms 36 each extend front-to-back beneath the seat portion 20, which is perhaps best seen in FIG. 5, although the numerous possibilities for the mounting thereto is well within the knowledge of those of ordinary skill in the art.

FIG. 2 illustrates some of the types of motion made possible by the structure of the lower mobility assembly 14 as previously described. The vertical supports 34, are capable of adjusting the height of the patient carrier by adjusting the relative positioning of the vertical arm uppers 34U and vertical arm lowers 34L as shown. In addition, forward and rearward tilting is accomplished by pivoting the U-arms 36 at their U-arm centers 36C with respect to the vertical support uppers 34U as shown by the U-arm 36 and numerous alternate positions therefor shown in phantom.

FIG. 3 illustrates how the patient carrier 12, is mounted upon the lower mobility assembly 14, whereby the seat portion 20 is mounted atop the ends 36E of the U-arms 36. FIG. 3 further illustrates how the patient carrier 12 can be tilted sideways. To effect a sideways tilt, the vertical supports 34 are adjusted so that they have different heights. Thus, one of the vertical supports 34 is made to have greater height than the other, so that the patient carrier 12 is tilted accordingly.

FIG. 4 illustrates how the patient carrier 12 can rotate about its central vertical axis. The lazy susan 32 is used to rotate the vertical supports 34, the U-arms 36, and thus the patient carrier supported thereby.

Referring once again to FIG. 5, several of the numerous positioning adaptations are illustrated. In particular, a removable pummel 50 is centrally located on the seat portion 20. When the patient is seated in the chair 10, the pummel is positioned between the patient's legs. Accordingly, the pummel 50 will prevent the patient from slouching downward in the chair. The pummel 50 thus has a large degree of effectiveness in keeping the patient upright, without the necessity of a less desirable alternative—a restraining belt.

Also seen in FIG. 5 are a plurality of removable support pillows 60. The pillows 60 are removable and positionable in a large variety of locations of the patient carrier front 12F in order to provide custom support to accommodate the particular needs of the patient.

Further seen in FIG. 5 are a pair of retractable leg supports 70. The retractable leg supports 70 selectively extending laterally outward from a leg support opening 72 in the calve support 24, extending parallel to said calve support 24. The retractable leg supports 70 help to support the leg of a patient which has a tendency to extend in a position other than directly in front of him.

Still further illustrated in FIG. 5 are a pair of multipositional arm rests 80. The multipositional arm rests 80 are hooked, having an elongated arm portion 82 with a broad top surface 84, and a wrist portion 85. With the hook shape, the multipositional arm rests 80 are configured so as to support the patient's arm with the elongated arm portion 82, and the patient's wrist with the wrist portion 85 which curves inward therefrom. The multipositional arm rests 80 can also be made to be removable, so that they can be removed if they interfere with the examination, or act as a hindrance to the comfort or support of the patient.

Lastly, illustrated in FIG. 5 is a central pillow 90 having a central pillow front 90F, mounted within a central pillow cavity 92 in the seat back 22, near the seat back top 22T. The central pillow 90 and central pillow cavity 92 is preferably in the shape of a smoothed figure eight, as seen in FIG. 5. The central pillow cavity 92 extends fully from the patient carrier front 12F to patient carrier rear 12R and is substantially the same size and shape as the central pillow 90. In FIG. 5, the central pillow is positioned wherein the central pillow front 90F is substantially coplanar with the patient carrier front 12F.

Figure 8:
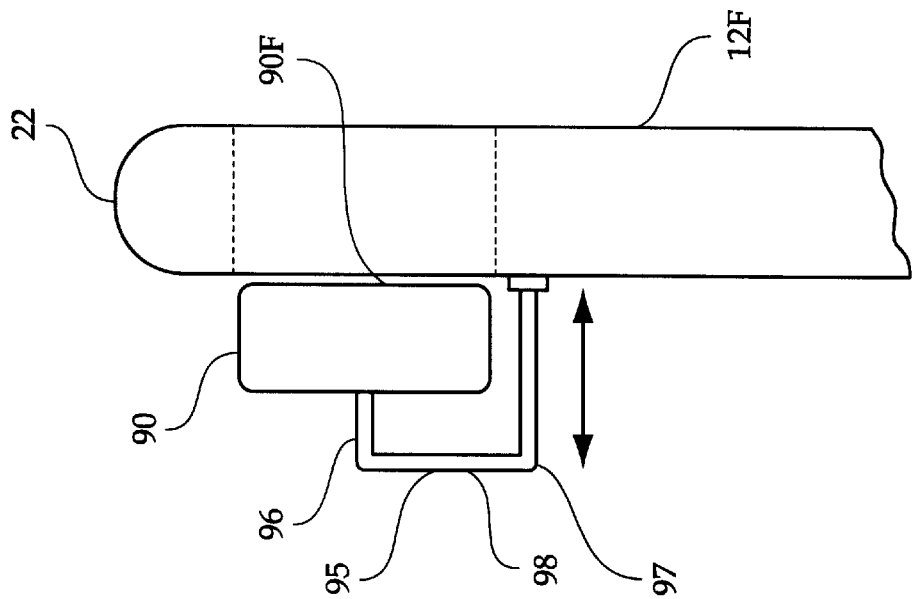
FIG. 8 is a side elevational view, similar to FIG. 7, except wherein the central pillow is retracted rearward of the patient carrier front.
Figure 7:
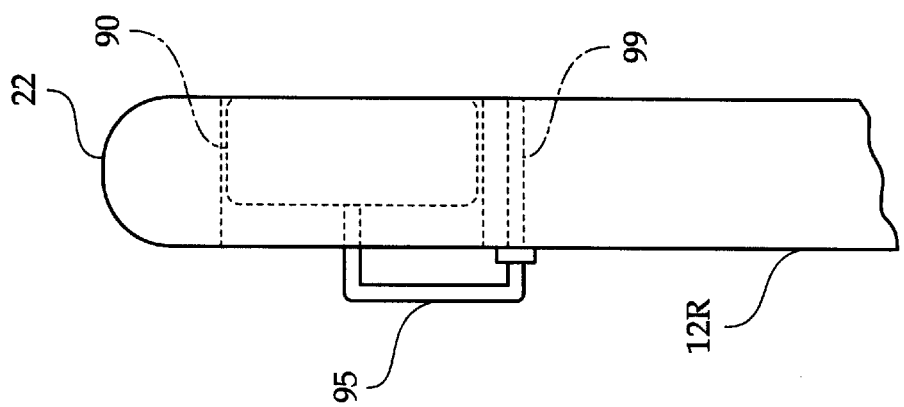
FIG. 7 is a side elevational view, illustrating the central pillow in a first position, wherein its front plane is substantially coplanar with the patient carrier front.

FIG. 7 and FIG. 8 are side elevational views of the seat back 22 which further illustrate the central pillow 90 and the mounting thereof. A mounting arm 95 is attached to the central pillow 90. The mounting arm 95 is unshaped, having a mounting arm upper member 96, a mounting arm lower member 97, and a mounting arm connecting member 98. The mounting arm upper member 96 extends perpendicularly behind the central pillow 90, and is rigidly affixed thereto. The mounting arm lower member 97 extends parallel to the mounting arm upper member 96, and is slidably mounted to the patient carrier, such that the mounting arm lower member 97 extends into a guide hole 99 in the patient carrier rear 12R. As illustrated in FIG. 7 and FIG. 8, the central pillow 90 can be positioned in multiple positions by sliding the mounting arm lower member 97 into or out of the guide hole 99, wherein its central pillow front 90F selectively extends coplanar with the patient carrier front 12F, or selectively extends in front of or behind the patient carrier front 12F. Thus the central pillow 90 is positionable where it can best provide support to the patient, or is out of the way where it does not interfere with the patient.

Figure 6:
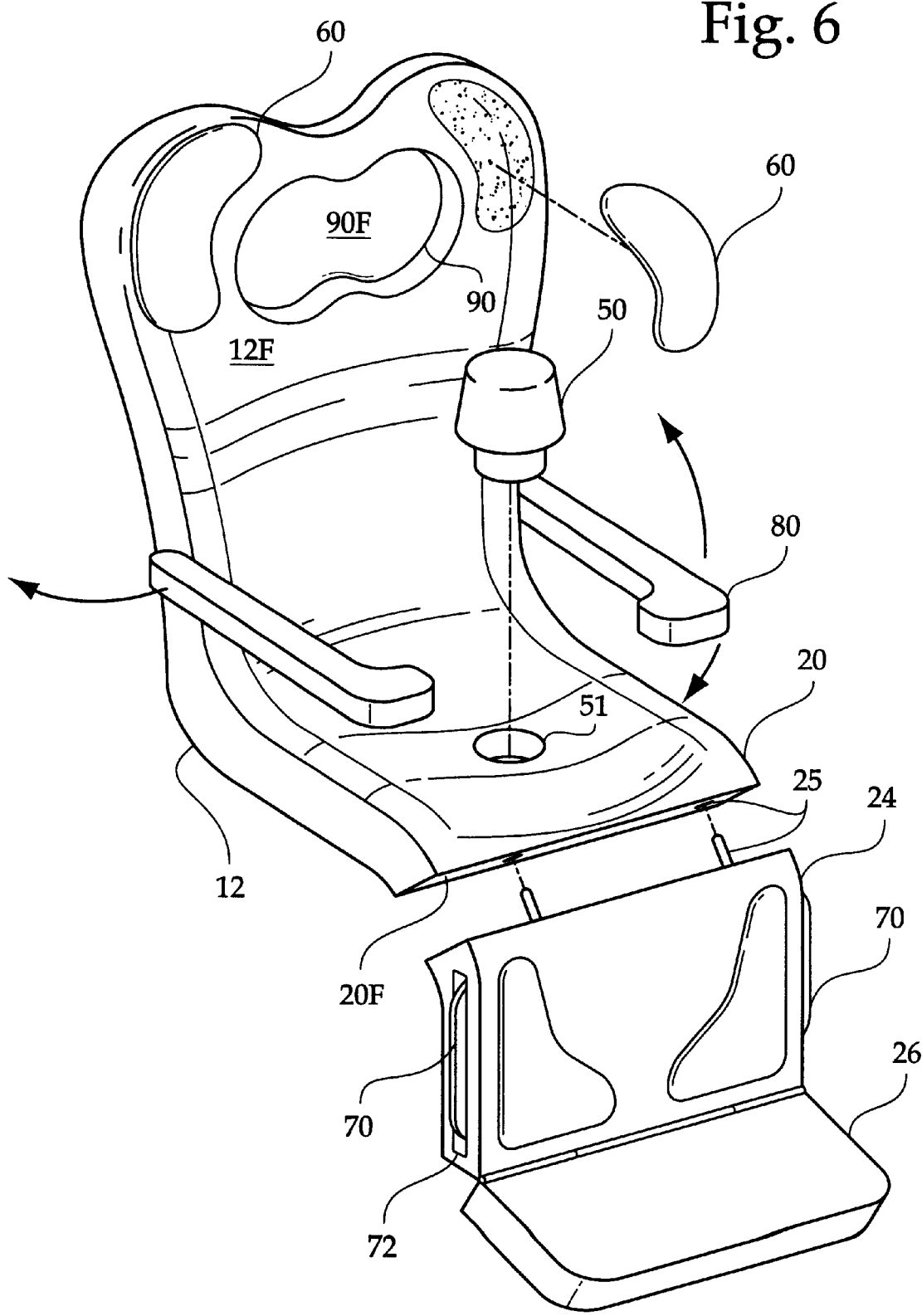
FIG. 6 is a diagrammatic perspective view, illustrating the patient carrier portion thereof, illustrating various positioning adaptations and use thereof.

Referring now to FIG. 6, further details regarding the adaptability and positionability of the patient carrier 12 are detailed. In particular, the pummel 50 is removably mounted in a pummel mount 51 which is centered on the seat portion 20. The removability of the pummel 50 allows it to be positioned once the patient is already seated in the chair. The pummel 50 can also be "removed" from its position wherein it protrudes from the patient carrier front 12F at the seat portion 20 by making said pummel 50 selectively retractable into the seat portion 20 such that it is recessed therebeneath.

Another detail depicted in FIG. 6 is the removability of the calve support 24 and foot rest 26 from the seat portion 20. As illustrated, the seat portion 20 has a seat portion front 20F, whereat the calve support 24 is normally substantially perpendicularly mounted thereto. However, a latching mechanism 25 may be employed to allow the calve support 24 to selectively detach from the seat portion 20. Detaching the calve support 24 and associated foot rest further enables the chair to adapt to the needs of different patients, as well as different purposes and medical procedures. The foot rest 26 is preferably hingeably mounted to the calve support 24 to facilitate compact storage thereof and provide further versatility for the present invention. Alternatively, the foot rest 26 can be configured as a lip which protrudes only a short distance from the calve support 24.

The retractable leg supports 70 are shown retracted in FIG. 6, wherein they are nearly fully retracted into the leg support openings 72 of the calve support 24. Also illustrated is the flexibility of the multipositional arm rests 80. The multipositional arm rests 80 are capable of pivoting upward and downward, as well as swinging inward and outward in a horizontal plane to either support the arms of the patient, or get out of the way as needed. Also seen in FIG. 6, the central support pillow 90 is retracted somewhat behind the patient carrier front 12F, so that the support pillow front 90F is somewhat behind the patient carrier front 12F.

Further, illustrated in FIG. 6 are the removability of the support pillows 60. As previously indicated, the pillows 60 are removable and positionable in a large variety of locations of the patient carrier front 12F, in order to provide custom support to accommodate the particular needs of the patient. To facilitate the removal and fastening to the patient carrier front 12F, hook and loop fastener material 19 is present on both the support pillows 60 and the patient carrier front 12F. In fact, hook or loop fastener material is preferably present on the greater portion of the patient carrier front 12F. Accordingly, when a support pillow 60 is necessary at a particular location of the patient carrier front 12F, it is simply adhered at said location. A plurality of support pillows 60 may be provided so as to have the greatest flexibility concerning the customization of the chair 10. Each of said support pillows 60 is preferably a gel-filled unit, to maximize comfort and durability. The support pillows 60, as well as the rest of the components of the x-ray chair 10 should be made of materials which are compatible with x-ray examinations, and materials which, if possible, tend not to obstruct or obscure the path of x-rays.

In conclusion, herein is provided a chair which facilitates accurate and useful x-ray examinations by providing optimal support and optimal comfort to a patient during the examinations. Numerous adaptations allow the chair to be customized to meet the needs of the patient and the medical examination being performed thereon.

The invention is illustrated by example in the accompanying drawing figures. However, it should be understood that these drawing figures merely provide a workable example of the inventive concepts. Accordingly, numerous variations and embodiments are possible while still adhering to the principles of the invention. Such variations are contemplated as being a part of the present invention.

What is claimed is:

1. An x-ray chair, for supporting a patient and providing comfort thereto during an x-ray examination, comprising:

a patient carrier, the patient carrier having a patient carrier front, a seat portion having a pummel mount centrally located thereon and having a seat portion front, a seat back attached to the seat portion, a calve support attached to the seat portion, the calve support having a pair of retractable leg supports which slide laterally outward from the calve support as needed so retract into the calve support when not needed, the patient carrier having a plurality of selectively attachable support pillows, the support pillows repositionable on the patient carrier front to provide needed support to the patient when seated in the chair;

a pummel, such that the pummel may be inserted into the pummel mount after the patient is seated in the chair to prevent the patient from slouching and sliding down the chair;

a foot rest hingeably attached to the calve support, wherein the calve support is detachable from the seat portion at the seat portion front;

a central pillow having a central pillow front, wherein the seat back has a seat back top and a central pillow cavity near the seat back top, the central pillow mounted in the central pillow cavity so that it is capable of selectively extending such that the central pillow front is coplanar with the patient carrier front, selectively extending such that the central pillow front is recessed behind the patient carrier front, and selectively extending such that the central pillow front extends in front of the patient carrier front;

a pair of multipositional arm rests, the multipositional arm rests capable of swinging outward and inward in a horizontal plane and capable of pivoting upward and downward, the multipositional arm rests are hooked, having an elongated arm portion with a broad top surface and a wrist portion; and a lower mobility assembly, the patient carrier mounted atop of the lower mobility assembly such that the lower mobility assembly gives the patient carrier the ability to raise and lower, rotate about a vertical axis, tilt forward and rearward, and tilt sideways, the lower mobility assembly having wheels for contacting a ground surface and providing lateral motion for the entire chair, the lower mobility assembly also having a base, the wheels are mounted to said base, further comprising a lazy susan mounted upon the base, two vertical supports mounted upon the lazy susan in diametrically opposed positions thereon, said vertical supports supporting the patient carrier.

2. The x-ray chair as recited in claim 1, wherein the lower mobility assembly further comprises a pair of u-arms, each u-arm having a u-arm center and a pair of u-arm ends, each u-arm mounted between one of the vertical supports and the patient carrier, such that each u-arm center is pivotally mounted to one of the vertical supports and the seat portion of the patient carrier is mounted onto the u-arm ends.

3. The x-ray chair as recited in claim 2, wherein each of the vertical supports has a vertical support upper and a vertical support lower, each of said vertical support uppers is adjustable with respect to it corresponding vertical support lower to adjust relative heights of the vertical supports to allow the patient carrier to tilt sideways.

* * * * *